US00PP25704P2

(12) United States Plant Patent
Nazeyrollas

(10) Patent No.: US PP25,704 P2
(45) Date of Patent: Jul. 14, 2015

(54) ***CEANOTHUS* PLANT NAMED 'MINMADORE'**

(50) Latin Name: ***Ceanothus delilianus*×*Caenothus pallidus***
Varietal Denomination: Minmadore

(71) Applicant: Olivier Nazeyrollas, Beaufort en Vallee (FR)

(72) Inventor: Olivier Nazeyrollas, Beaufort en Vallee (FR)

( * ) Notice: Subject to any disclaimer, the term of this patent is extended or adjusted under 35 U.S.C. 154(b) by 70 days.

(21) Appl. No.: 13/998,432

(22) Filed: Oct. 31, 2013

(51) Int. Cl.
*A01H 5/00* (2006.01)

(52) U.S. Cl.
USPC ..... Plt./226

(58) Field of Classification Search
USPC ..... Plt./226
CPC ..... A01H 5/00
See application file for complete search history.

*Primary Examiner* — Kent L Bell
(74) *Attorney, Agent, or Firm* — C. A. Whealy

(57) ABSTRACT

A new and distinct cultivar of *Ceanothus* plant named 'Minmadore', characterized by its upright and compact plant habit; freely branching habit; yellow green-colored leaves; numerous pink-colored flowers; and good garden performance especially in shaded areas.

4 Drawing Sheets

Botanical designation: *Ceanothus delilianus*×*Ceanothus pallidus*.

Cultivar denomination: 'MINMADORE'.

BACKGROUND OF THE INVENTION

The present invention relates to a new and distinct *Ceanothus* plant, botanically known as *Ceanothus delilianus*× *Ceanothus pallidus* and hereinafter referred to by the name 'Minmadore'.

The new *Ceanothus* plant is a naturally-occurring branch mutation of *Ceanothus delilianus*×*Ceanothus pallidus* 'Minmarose', not patented. The new *Ceanothus* plant was discovered and selected by the Inventor in July, 2008 on a single plant of 'Minmarose' within a population of plants of 'Minmarose' in a controlled environment in Maine et Loire, France.

Asexual reproduction of the new *Ceanothus* plant by cuttings in a controlled environment in Maine et Loire, France since August, 2008 has shown that the unique features of this new *Ceanothus* plant are stable and reproduced true to type in successive generations of asexual reproduction.

SUMMARY OF THE INVENTION

Plants of the new *Ceanothus* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Minmadore'. These characteristics in combination distinguish 'Minmadore' as a new and distinct *Ceanothus* plant:

1. Upright and compact plant habit.
2. Freely branching habit.
3. Yellow green-colored leaves.
4. Numerous pink-colored flowers.
5. Good garden performance especially in shaded areas.

Plants of the new *Ceanothus* can be compared to plants of the mutation parent, 'Minmarose'. Plants of the new *Ceanothus* differ from plants of 'Minmarose' in the following characteristics:

1. Plants of the new *Ceanothus* are more compact than plants of 'Minmarose'.
2. Plants of the new *Ceanothus* are not as vigorous as plants of 'Minmarose'.
3. Plants of the new *Ceanothus* are not as freely branching as plants of 'Minmarose'.
4. Plants of the new *Ceanothus* have yellow green-colored leaves whereas plants of 'Minmarose' have green-colored leaves.
5. Plants of the new *Ceanothus* have smaller inflorescences with fewer flowers than plants of 'Minmarose'.

Plants of the new *Ceanothus* can be compared to plants of *Ceanothus pallidus* 'Marie Simon', not patented. In side-by-side comparisons conducted in Maine et Loire, France, plants of the new *Ceanothus* differed from plants of 'Marie Simon' in the following characteristics:

1. Plants of the new *Ceanothus* had yellow green-colored leaves whereas plants of 'Marie Simon' had dark green-colored leaves.
2. Plants of the new *Ceanothus* and 'Marie Simon' differed in stem color.
3. Plants of the new *Ceanothus* had more open (less dense) inflorescences than plants of 'Marie Simon'.

BRIEF DESCRIPTION OF THE PHOTOGRAPHS

The accompanying colored photographs illustrate the overall appearance of the new *Ceanothus* plant showing the colors as true as it is reasonably possible to obtain in colored reproductions of this type. Colors in the photographs may differ slightly from the color values cited in the detailed botanical description which accurately describe the colors of the new *Ceanothus* plant.

The photograph on the first sheet is a side perspective view of a typical vegetative plant of 'Minmadore' grown in an outdoor nursery.

The photograph on the second sheet is a close-up view of typical leaves of 'Minmadore'.

The photograph on the third sheet is a close-up view of typical inflorescences of 'Minmadore'.

The photograph on the fourth sheet comprises close-up views of typical flowering plants of 'Minmadore' (left) and 'Minmarose' (right).

DETAILED BOTANICAL DESCRIPTION

The aforementioned photographs and following observations, measurements and values describe plants grown during the summer and early autumn in ground beds and 4.5-liter containers in a shadehouse in Maine et Loire, France and under cultural practices typical of commercial *Ceanothus* production. During the production of the plants, day temperatures averaged 16° C. and night temperatures averaged 9° C. Plants were three years old when the photographs and the description were taken. In the description, color references are made to The Royal Horticultural Society Colour Chart, 2001 Edition, except where general terms of ordinary dictionary significance are used.

Botanical classification: *Ceanothus delilianus*×*Ceanothus pallidus* 'Minmadore'.

Parentage: Naturally-occurring branch mutation of *Ceanothus delilianus*×*Ceanothus pallidus* 'Minmarose', not patented.

Propagation:

*Type*.—By cuttings.

*Time to initiate roots, summer*.—About one month at 18° C.

*Time to produce a rooted young plant, summer*.—About three months at 18° C.

*Root description*.—Fine, fleshy; white in color.

*Rooting habit*.—Freely branching; dense.

Plant description:

*Plant and growth habit*.—Perennial deciduous shrub; upright and compact plant habit; moderately vigorous growth habit.

*Branching habit*.—Freely branching habit with about 15 lateral branches developing per plant; bushy appearance.

*Plant height*.—About 28 cm.

*Plant diameter* (*area of spread*).—About 36 cm.

Lateral branch description:

*Length*.—About 28 cm.

*Diameter*.—About 2 mm.

*Internode length*.—About 2 cm.

*Texture*.—Pubescent.

*Strength*.—Strong, flexible.

*Color*.—Close to N144D and 178B.

Leaf description:

*Arrangement*.—Alternate, simple.

*Length*.—About 6.6 cm.

*Width*.—About 3.4 cm.

*Shape*.—Elliptic.

*Apex*.—Acute.

*Base*.—Obtuse.

*Margin*.—Serrate.

*Texture, upper surface*.—Smooth, glabrous.

*Texture, lower surface*.—Pubescent.

*Venation pattern*.—Pinnate.

*Color*.—Developing leaves, upper surface: Close to 151A. Developing leaves, lower surface: Close to 151B. Fully expanded leaves, upper surface: Close to 144A; venation, similar to lamina color. Fully expanded leaves, lower surface: Close to 144B; venation, similar to lamina color.

*Petioles*.—Length: About 8 mm. Diameter: About 1 mm. Texture, upper and lower surfaces: Smooth, glabrous. Color, upper and lower surfaces: Close to 145A.

Flower description:

*Flower appearance and arrangement*.—Single flowers arranged in panicles; panicles roughly hemispherical in shape; freely flowering habit with usually about 157 flowers developing per inflorescence; flowers face mostly upright.

*Natural flowering season*.—Plants flower continuously from July through October in France; flowers not persistent.

*Fragrance*.—Light; sweet, honey-like.

*Inflorescence height*.—About 4.5 cm.

*Inflorescence diameter*.—About 5 cm.

*Flower diameter*.—About 5 mm.

*Flower length* (*height*).—About 5 mm.

*Flower buds*.—Length: About 1 mm. Diameter: About 2 mm. Shape: Flattened globular. Color: Close to 65B.

*Petals*.—Quantity and arrangement: Five petals in a single whorl. Length: About 3 mm. Width: About 1 mm. Shape: Spatulate. Apex: Rounded. Margin: Entire. Texture, upper and lower surfaces: Smooth, glabrous. Color: When opening, upper and lower surfaces: Close to 65B. Fully opened, upper and lower surfaces: Close to 65C; color becoming closer to 75B with development.

*Sepals*.—Quantity and arrangement: Five in a single whorl. Length: About 1 mm. Width: About 2 mm. Shape: Ovate. Apex: Acute. Base: Truncate. Margin: Entire. Texture, upper and lower surfaces: Smooth, glabrous. Color, upper and lower surfaces: Close to 65B.

*Peduncles*.—Length: About 3 cm. Diameter: About 1 mm. Strength: Strong; flexible. Texture: Smooth, glabrous. Color: Close to N144D and 178B.

*Pedicels*.—Length: About 1 cm. Diameter: About 0.5 mm. Strength: Strong; flexible. Texture: Smooth, glabrous. Color: Close to 65A.

*Reproductive organs*.—Androecium: Quantity per flower: Five. Filament length: About 2 mm. Filament color: Close to 62D. Anther length: About 0.5 mm. Anther shape: Globular. Anther color: Yellow. Pollen color: Yellow. Gynoecium: Quantity per flower: One. Pistil length: About 3 mm. Style length: About 2 mm. Style color: Close to N66C. Stigma shape: Tri-parted. Stigma color: Close to N66C. Ovary color: Close to N66C.

*Fruits*.—Length: About 3 mm. Diameter: About 4 mm. Color, mature: Close to N34A.

Garden performance: Plants of the new *Ceanothus* have been observed to have good garden performance and to tolerate rain, wind and temperatures ranging from about −10° C. to about 40° C. To avoid sun scalding of the leaves, garden performance of plants of the new *Ceanothus* is optimal in shaded areas.

Pathogen & pest resistance: Plants of the new *Ceanothus* have not been observed to be resistant to pathogens and pests common to *Ceanothus* plants.

It is claimed:

1. A new and distinct *Ceanothus* plant named 'Minmadore' as illustrated and described.

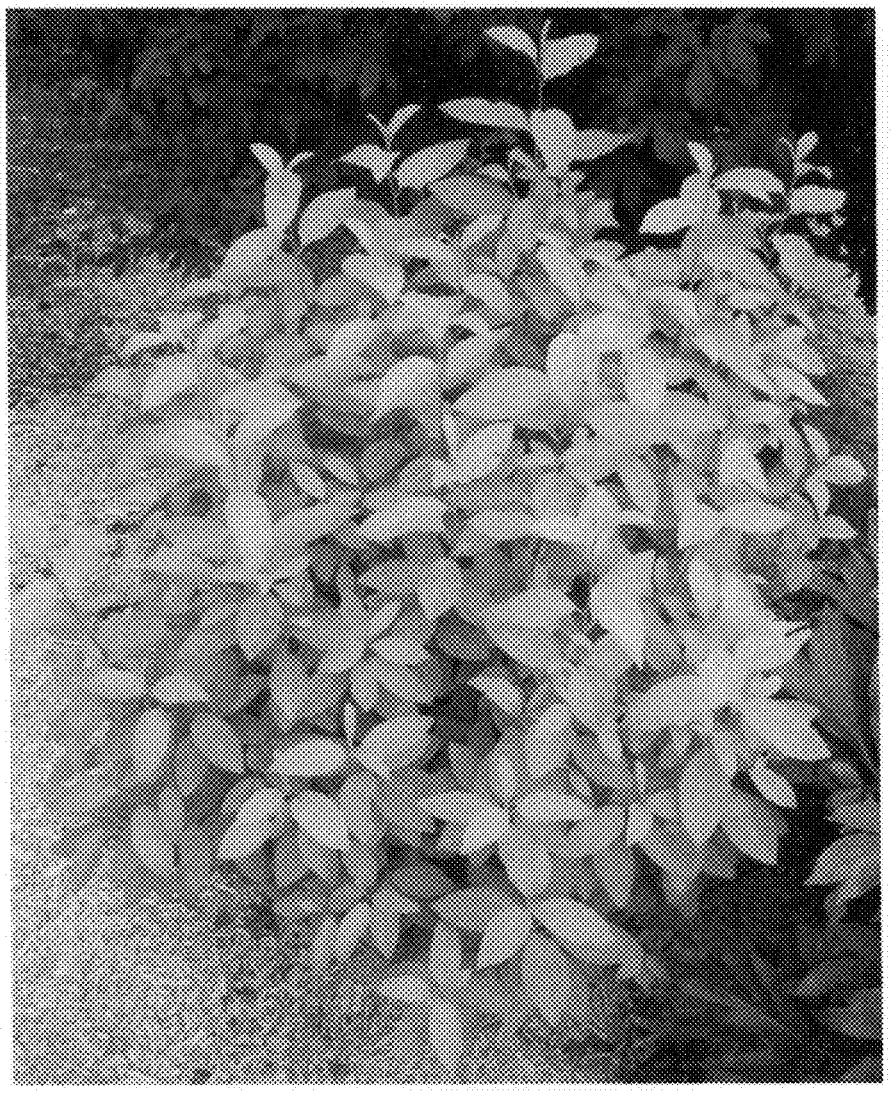

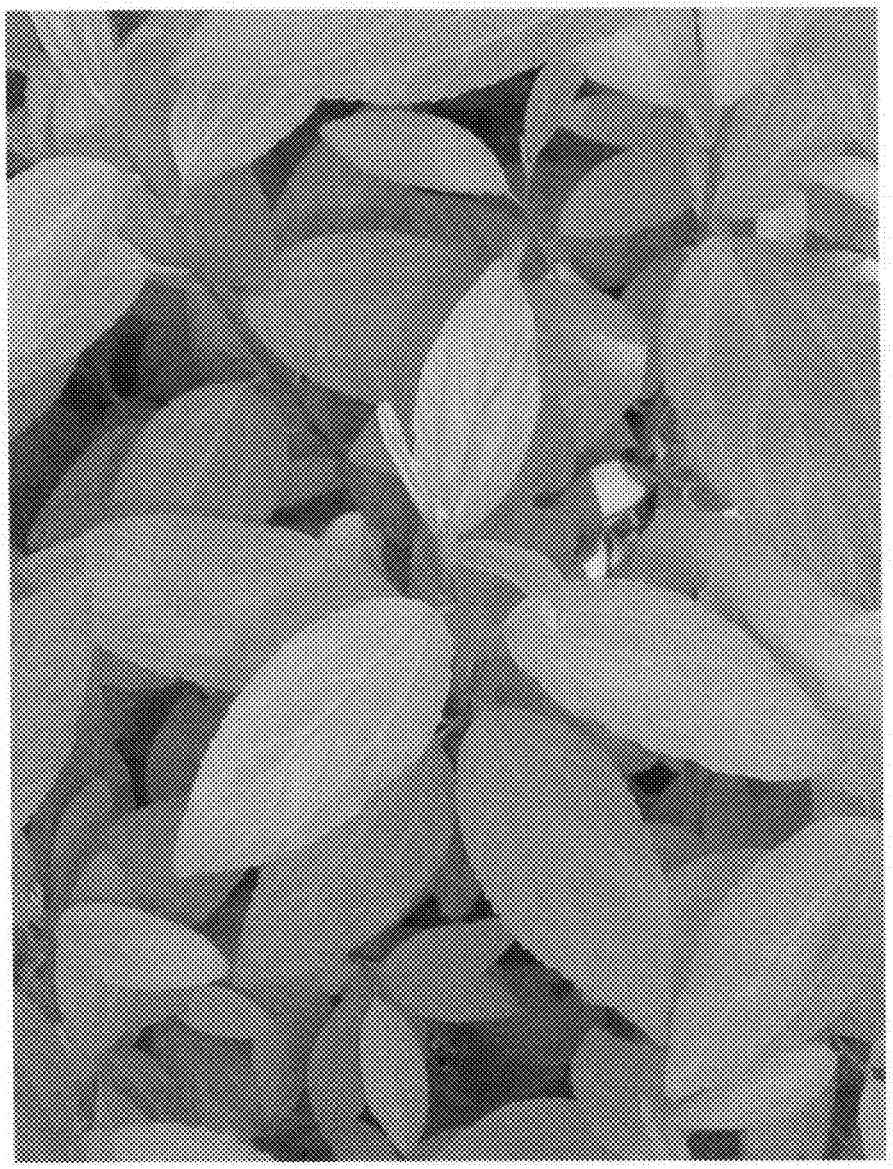

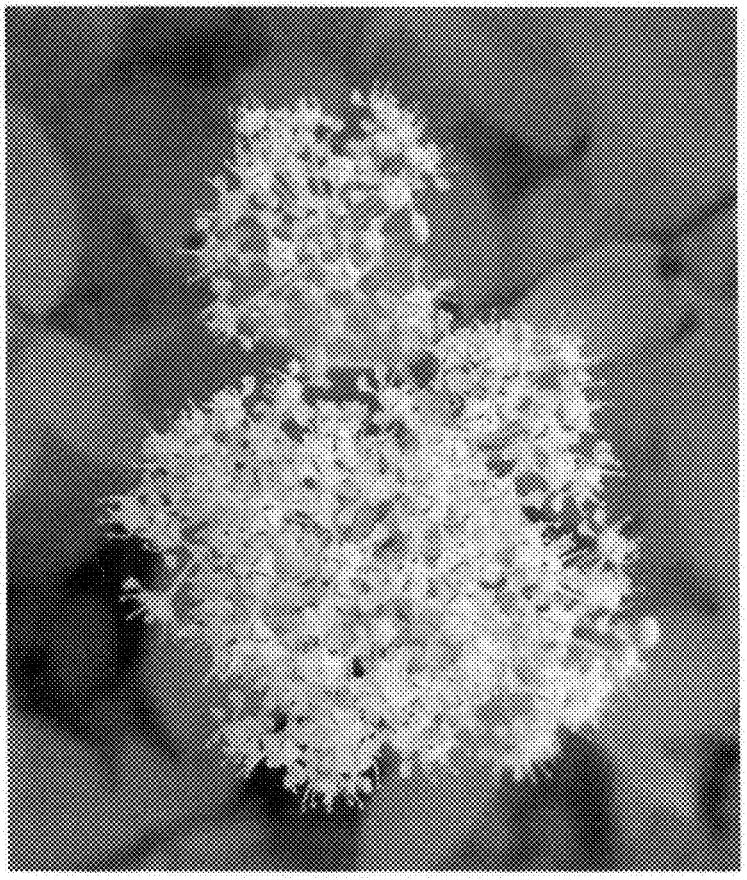

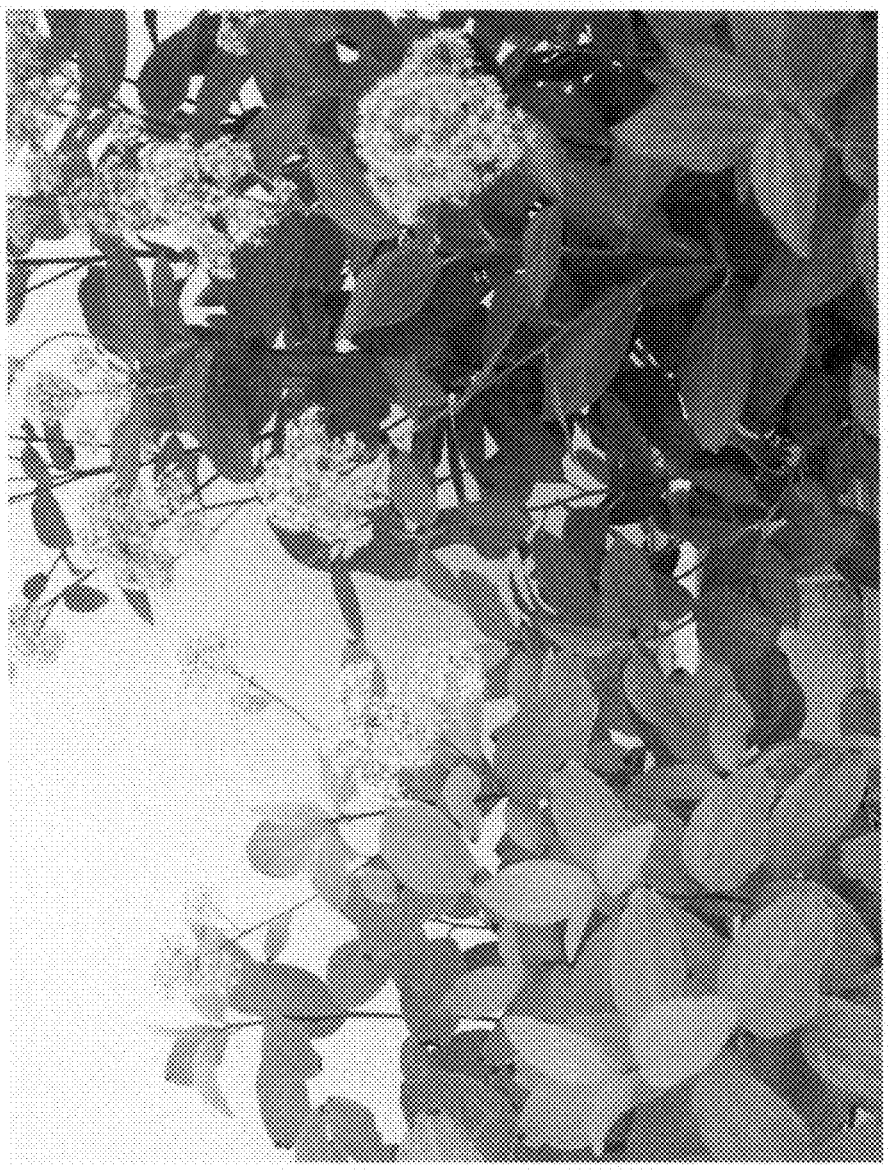

* * * * *